United States Patent
Akutsu

(10) Patent No.: US 9,201,085 B2
(45) Date of Patent: Dec. 1, 2015

(54) AUTOMATIC ANALYZING DEVICE

(75) Inventor: Masashi Akutsu, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 13/515,356

(22) PCT Filed: Dec. 3, 2010

(86) PCT No.: PCT/JP2010/007042
§ 371 (c)(1),
(2), (4) Date: Jun. 12, 2012

(87) PCT Pub. No.: WO2011/074202
PCT Pub. Date: Jun. 23, 2011

(65) Prior Publication Data
US 2012/0251389 A1    Oct. 4, 2012

(30) Foreign Application Priority Data
Dec. 15, 2009 (JP) ................................. 2009-283570

(51) Int. Cl.
*G01N 35/00* (2006.01)
*G01N 35/04* (2006.01)

(52) U.S. Cl.
CPC ............ *G01N 35/04* (2013.01); *G01N 35/0092* (2013.01); *G01N 2035/0465* (2013.01)

(58) Field of Classification Search
None
See application file for complete search history.

(56) References Cited

U.S. PATENT DOCUMENTS

| 5,490,321 A | 2/1996 | Kaneko |
| 5,628,962 A * | 5/1997 | Kanbara et al. ................. 422/63 |
| 2005/0013742 A1* | 1/2005 | Shaw ............................... 422/99 |
| 2005/0207938 A1* | 9/2005 | Hanawa et al. .................. 422/64 |
| 2006/0177344 A1* | 8/2006 | Ouchi et al. ..................... 422/64 |
| 2008/0085215 A1* | 4/2008 | Mototsu et al. .............. 422/68.1 |
| 2008/0199358 A1 | 8/2008 | Yamano |

FOREIGN PATENT DOCUMENTS

| JP | 01/229975 A | 9/1989 |
| JP | 04-036658 A | 2/1992 |
| JP | 06-324051 A | 11/1994 |

(Continued)

OTHER PUBLICATIONS

Chinese Office Action received in Chinese Application No. 201080057075.3 dated Sep. 23, 2013.

*Primary Examiner* — Jill Warden
*Assistant Examiner* — Julie Tavares
(74) *Attorney, Agent, or Firm* — Mattingly & Malur, PC

(57) ABSTRACT

A reagent loading mechanism includes a reagent loading unit and a reagent holding unit serving as a rotating mechanism. A reagent cover opening mechanism and a reagent transferring mechanism are disposed on the circumference of the reagent holding unit. A position at which the reagents can be continuously loaded from the reagent loading unit can be selected from accommodating positions in the reagent holding unit by setting the number (X) of held reagents and an offset number (Y) of the opening mechanism and the transferring mechanism to satisfy a relationship of X=nY+1 (n is arbitrary). In addition, the opening operation and the transferring operation are performed during the same period so that unnecessary operations of the mechanisms can be suppressed by controlling the sequence such that opening of the reagent covers and transferring of the reagents can be continuously performed.

12 Claims, 10 Drawing Sheets

(56) References Cited

FOREIGN PATENT DOCUMENTS

| JP | 2005-37171 | A | 2/2005 |
| JP | 2007-303882 | A | 11/2007 |
| JP | 2008-203004 | A | 9/2008 |
| JP | 2009-068992 | A | 4/2009 |

* cited by examiner

AUTOMATIC ANALYZING DEVICE

The present application is the U.S. National Phase of International Application No. PCT/JP2010/007042, filed Dec. 3, 2010, which claims the benefit of Japanese Patent Application No. 2009-283570, filed Dec. 15, 2009, the entire contents of which are hereby incorporated by reference.

TECHNICAL FIELD

The present invention relates to an automatic analyzing device that performs quantitative and qualitative analysis of biogenic samples including blood and urine. In particular, the present invention relates to an automatic analyzing device having a replacement reagent container holding mechanism that holds a plurality of replacement reagent containers.

BACKGROUND ART

In general, automatic analyzing devices, which automatically perform quantitative and qualitative analysis of biogenic samples including blood and urine, are provided with a reagent container repository on the device that keeps a plurality of reagents corresponding to analysis items, in order to enable measuring a plurality of analysis items. The reagent container repository is managed by a person in charge of management of the device so that a reagent necessary for analysis for one day is kept therein, and in the event of occurrence of reagent shortage during the analysis, the analysis is once interrupted for reagent replacement.

On the other hand, the number of items analyzed by the automatic analyzing device has been increasing, and in order to deal with analysis of other items, it is common to downsize one reagent container to thereby allow placement of many reagent containers. In this case, as compared to conventional devices, it is more likely that the reagent runs short during the analysis. Therefore, an automatic analyzing device having a mechanism that can automatically add a reagent in a reagent container repository is described in Patent Literature 1.

CITATION LIST

Patent Literature

Patent Literature 1: Japanese Patent Laid-Open Publication No. 2008-203004

SUMMARY OF INVENTION

Technical Problem

While the automatic analyzing device described in Patent Literature 1 allows automated reagent addition during analysis, it is not provided with a function to automatically open the reagent cover. Therefore, it has been required to dispose the reagent container in the reagent loading mechanism with the reagent cover having been opened in advance.

When the reagent cover is left open, the reagent in the reagent container vaporizes to change the concentration of the reagent, and as a result of that, measurement might be unstable.

Further, since the reagent loading operation requires the reagent container repository to temporarily stop, it is necessary to shorten the time of stop as far as possible.

Further, since the reagent container itself is to be moved, lowering the operation speed of the mechanism as far as possible to prevent bubbling or rolling of the liquid surface of the reagent within the container can result in prevention of changes in the concentration of the reagent, as well as stabilizing the results of measurements.

In other words, it is necessary to keep the reagent cover unopened in stand-by until the reagent is needed, and at the timing when it is determined that reagent is needed, the cover is opened to rapidly dispose the reagent within the reagent repository of analyzing device, and it is necessary that the number of times of operation by the mechanism is reduced as far as possible.

Solution to Problem

A reagent loading mechanism is divided into a reagent loading unit and a loaded reagent holding unit, and the loaded reagent holding unit is configured as a rotating mechanism. Further, on the circumference of the loaded reagent holding unit, a reagent cover opening mechanism and a reagent transportation unit are provided, so that opening of the held reagent to the movement thereof to a transportation unit can be performed in series.

Further, on assumption that reagents are loaded in succession, by selecting positions in which reagents can be successively loaded among accommodation positions in the reagent holding unit when the reagents are loaded from the reagent loading unit, it is possible to perform opening the reagent and transportation continuously and at a same period.

Advantageous Effects of Invention

According to the present invention, by preparing reagents necessary for analysis performed in one day, it is possible not only to allow continuous analysis without a halt of the device but to prevent reagent evaporation of the reagents to a maximum extent.

Furthermore, it is possible to reduce the time for reagent replacement to a maximum extent while preventing bubbling or rolling of the liquid surface of the reagent.

DESCRIPTION OF EMBODIMENTS

Figure 1:
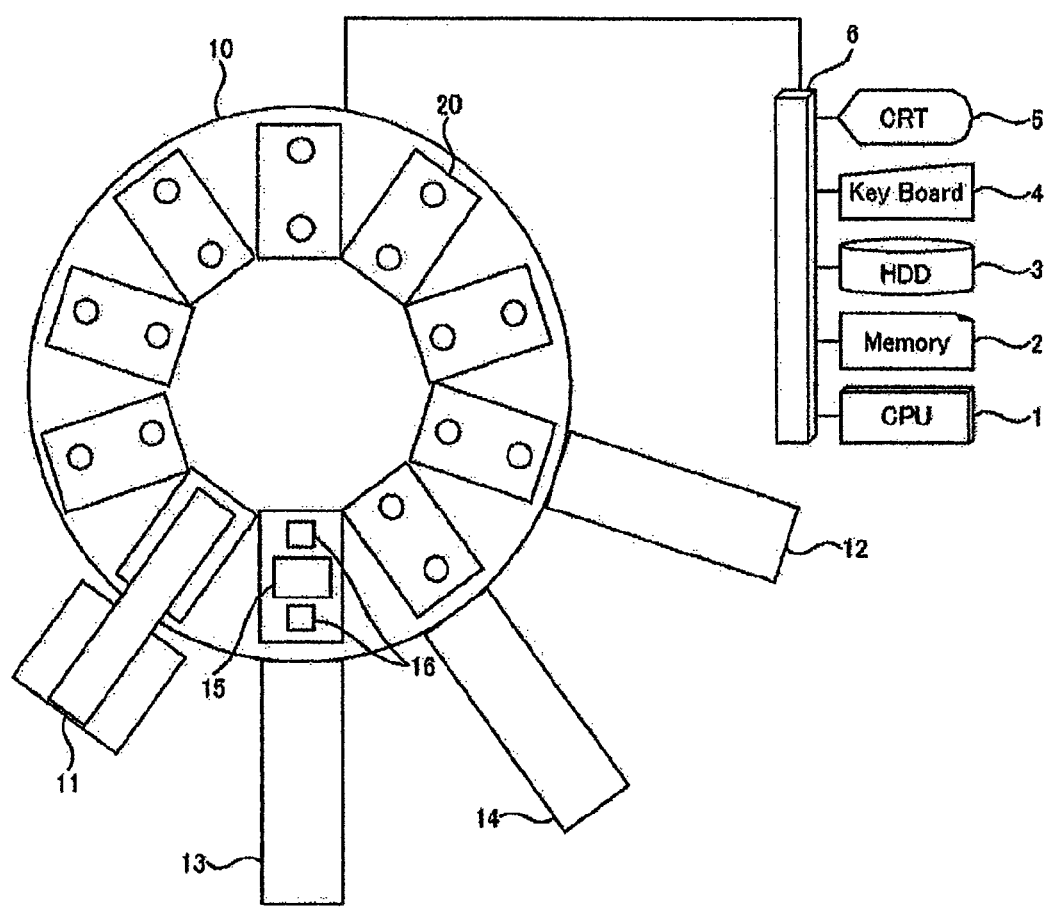
FIG. 1 is a configuration diagram of an automatic analyzing device according to one embodiment of the present invention.

FIG. 1 is a configuration diagram showing one embodiment of the device of the present invention, that is, a configuration diagram showing as a whole the configuration of multiitem chemical analyzing device that analyzes a plurality of analysis items of a specimen sample by using a photometric measurement scheme.

In FIG. 1, a reagent cover opening mechanism 11, a reagent container loading mechanism 13, a reagent discarding mechanism 14 and a reagent replacement position transferring mechanism 12 are radially arranged with respect to a replacement reagent container holding mechanism 10. The operations of reagent cover opening mechanism 11, the reagent container loading mechanism 13, the reagent discarding mechanism 14, the reagent replacement position transferring mechanism 12, and the replacement reagent container holding mechanism 10 are controlled via an interface 6 by a microcomputer 1 that performs operation control of each unit of the mechanisms and computation of measurement data.

The reagent cover opening mechanism 11 opens the cover of the replacement reagent container disposed on the replacement reagent container holding mechanism 10. The reagent replacement position transferring mechanism 12 transports a reagent container disposed on the replacement reagent container holding mechanism 10 to other reagent container holding mechanisms or analysis units that are not illustrated. The reagent container loading mechanism 13 loads the replacement reagent container 20 to the replacement reagent container holding mechanism 10 from the outside. The reagent discarding mechanism 14 discards the reagent container on the replacement reagent container holding mechanism 10.

In the present embodiment, within the replacement reagent container holding mechanism 10, 10 (ten) number at the maximum of the replacement reagent containers 20 can be on stand-by.

Figure 2:
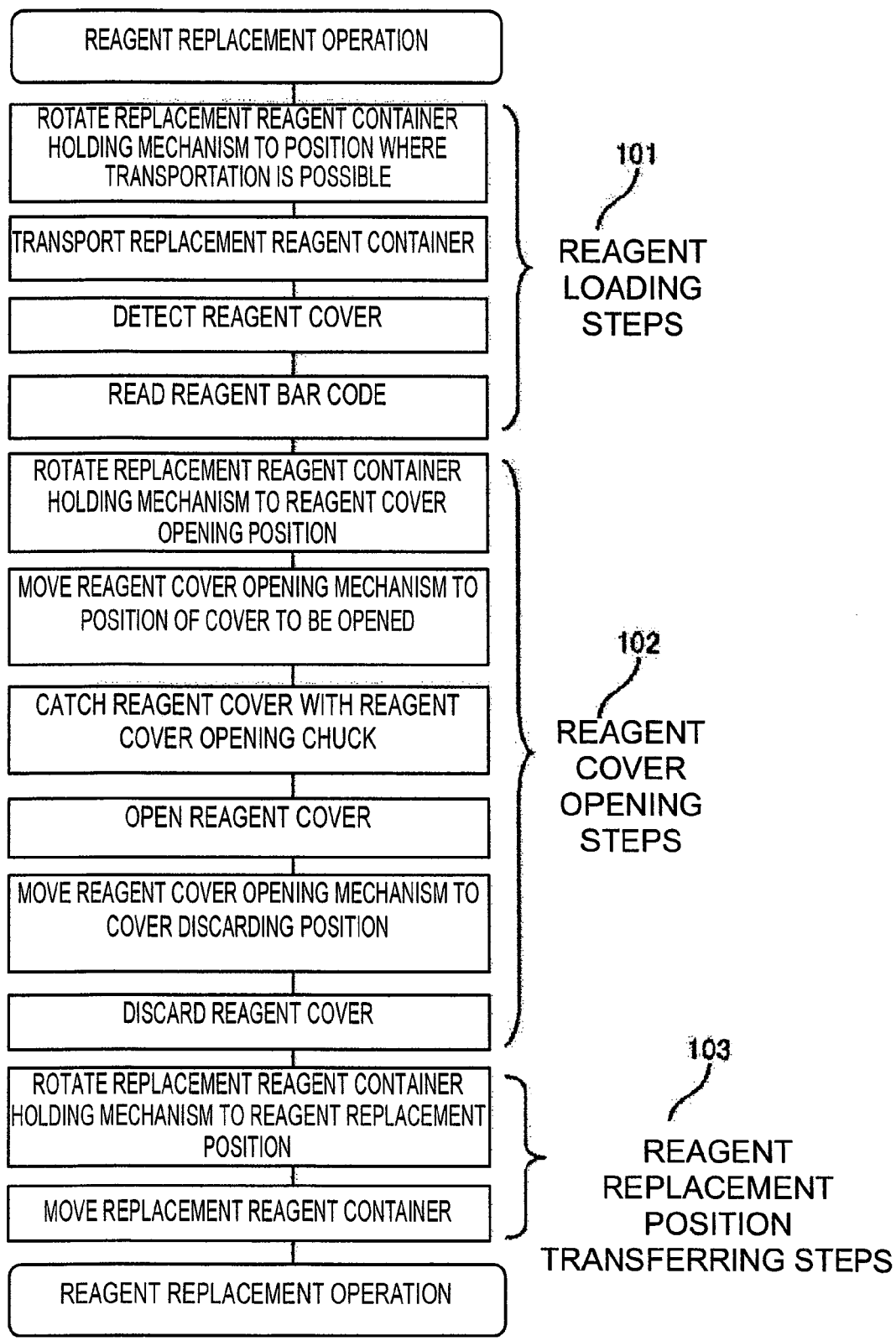
FIG. 2 shows steps of a reagent replacement operation.

As shown in FIG. 2, as a normal reagent replacement operation, reagent loading steps 101, reagent cover opening steps 102, and reagent replacement position transferring steps 103 take place in this order.

Figure 3:
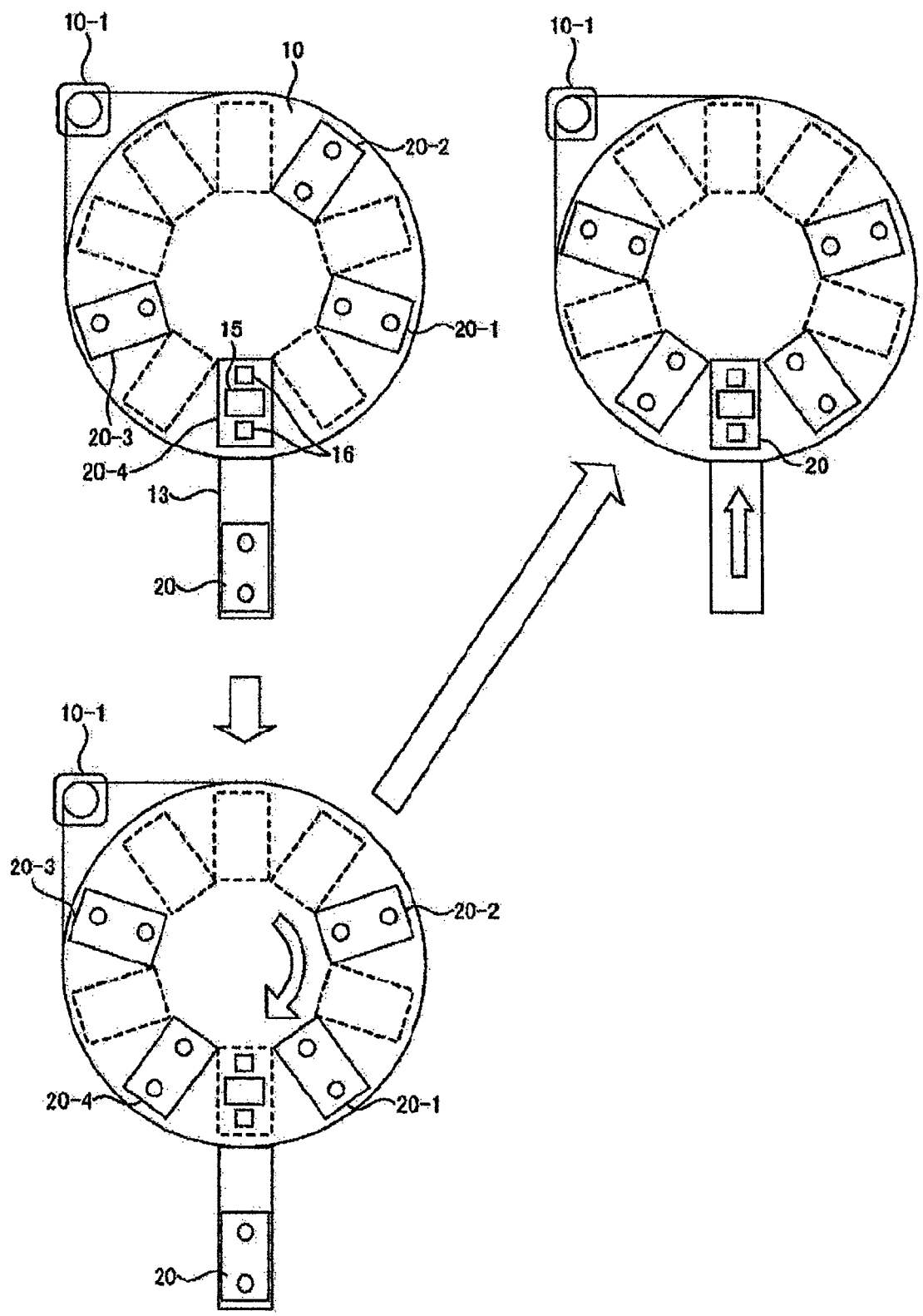
FIG. 3 shows an operation of reagent loading steps.

In the reagent loading steps 101 shown in FIG. 3, at the time point when the disposed replacement reagent container 20 is recognized, the replacement reagent container holding mechanism 10 is rotationally transferred so that the reagent container loading mechanism 13 and the replacement position where the accommodation is possible within the replacement reagent container holding mechanism 10 are on a straight line. This replacement reagent container holding mechanism 10 is rotated by the replacement reagent container holding mechanism driving motor 10-1. Next, the replacement reagent container 20 is moved inside the replacement reagent container holding mechanism 10. Having moved inside the replacement reagent container holding mechanism 10, the reagent container 20 is subjected to reading of the opening status of the reagent cover 22 on the replacement reagent container and reading of the reagent bar code 21 on the replacement reagent container by the reagent cover detection mechanism 16 and the reagent bar code reading mechanism 15. The information appendant to the reagent is compared with information within the external storage medium 3 via the interface 6, and when it is determined that the replacement reagent container 20 can be used, the device places the reagent container 20 in the replacement reagent holding mechanism 10 in sand-by. When it is determined that the reagent container 20 is unusable, the device rotates the replacement reagent holding mechanism 10 to be on a straight line with the reagent discarding mechanism 14 and the reagent container 20 is discarded via the reagent discarding mechanism 14.

Figure 4:
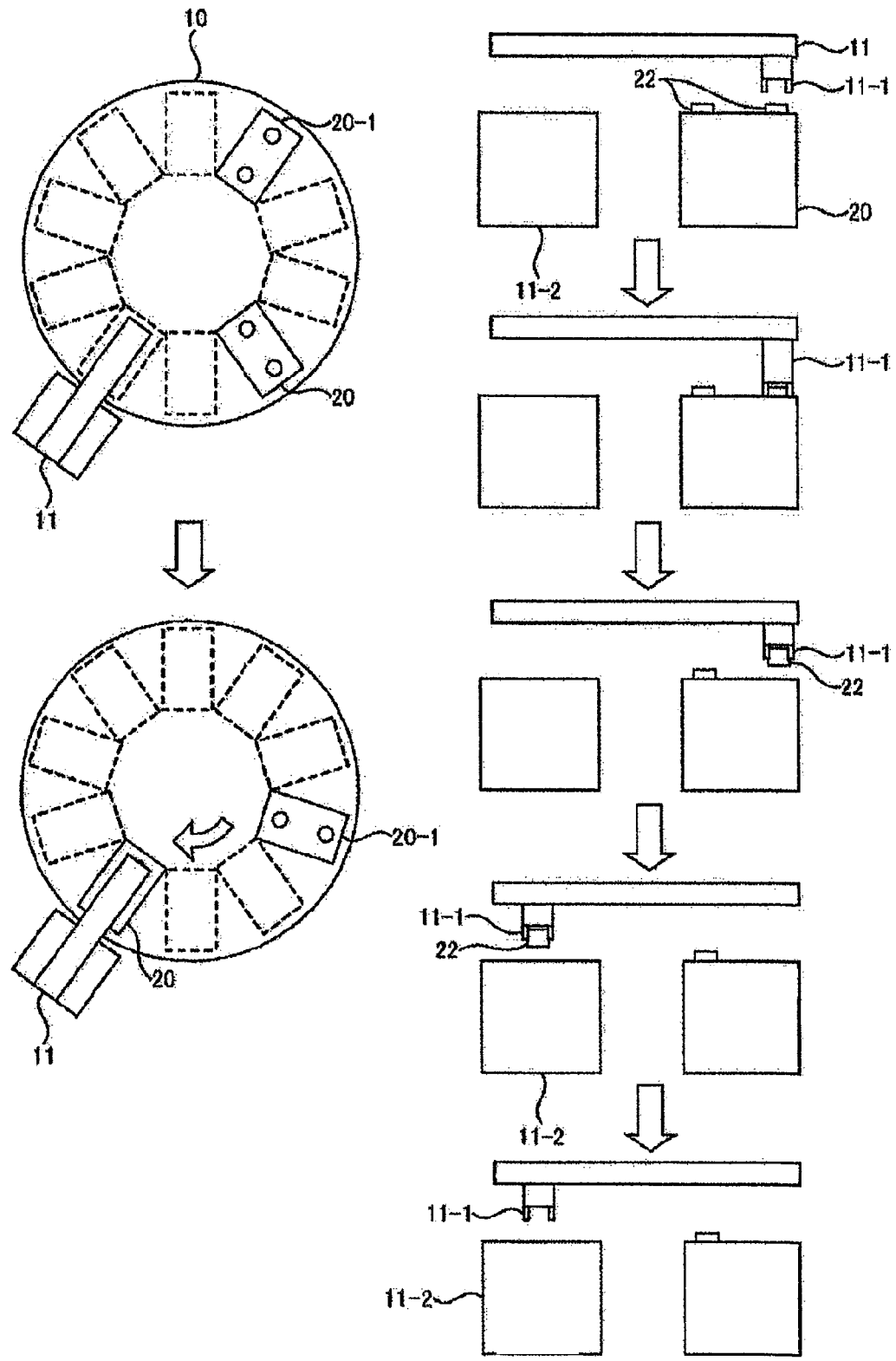
FIG. 4 shows an operation of reagent cover opening steps.

In the reagent cover opening steps 102 shown in FIG. 4, the replacement reagent container holding mechanism 10 is rotated so that the standby positions of the reagent cover opening mechanism 11 and replacement reagent container 20 to be opened within the replacement reagent container holding mechanism 10 are on a straight line. Next, the reagent cover opening mechanism 11 is moved on the reagent cover 22 of the replacement reagent container 20. The reagent cover opening chuck 11-1 is moved down to catch the reagent cover 22. The reagent cover opening chuck 11-1 in the state of having caught the reagent cover 22 is raised to remove the reagent cover 22 from the replacement reagent container 20. The reagent cover opening mechanism 11 is moved to the position above the reagent cover discarding box 11-2 and releases the reagent cover 22 from the reagent cover opening chuck 11-1.

As described above, it is possible to perform the opening operation. In the drawings, although two reagent covers are depicted, any number of one or more reagent covers may be used.

Figure 5:
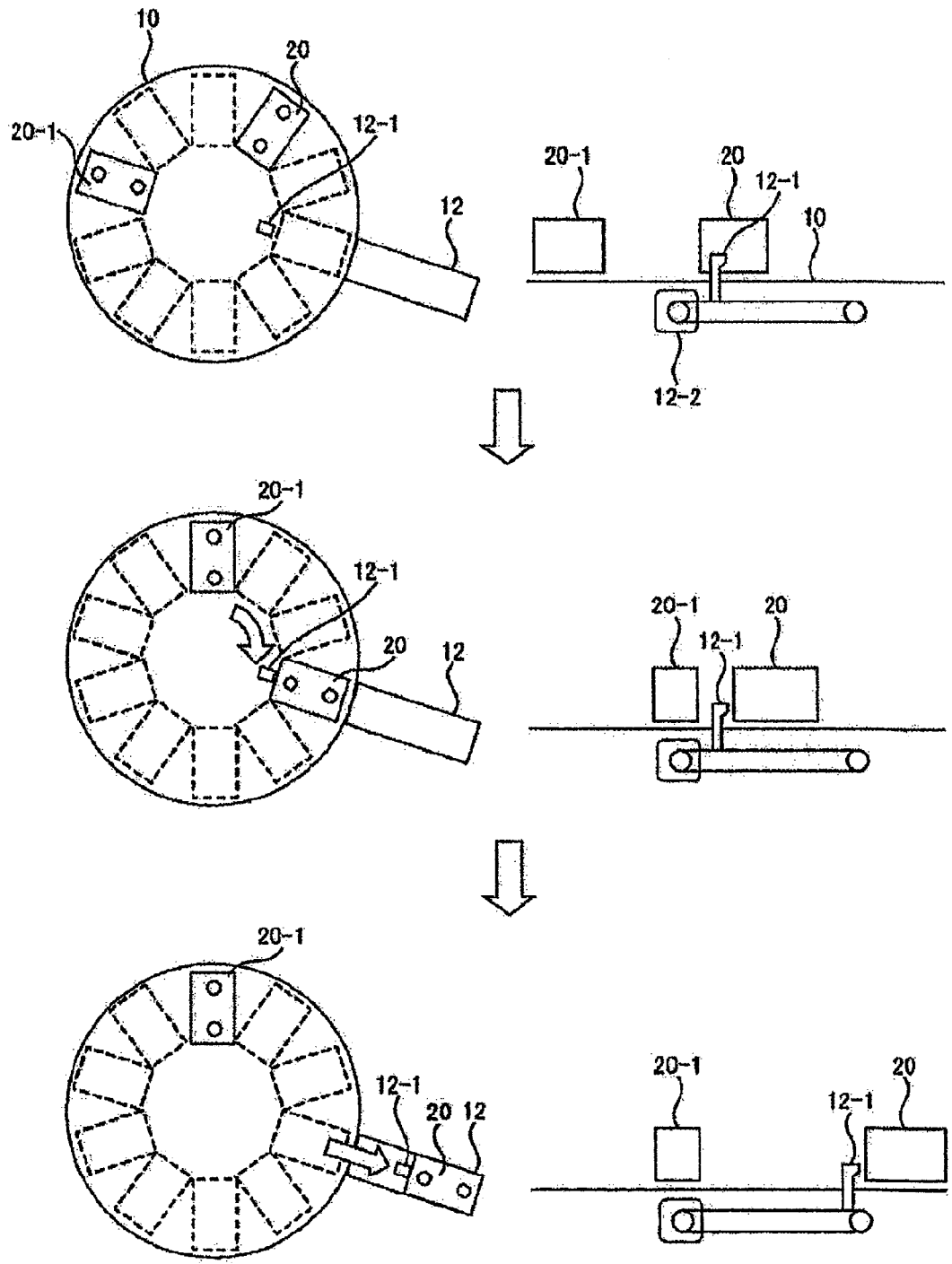
FIG. 5 shows an operation of reagent transferring steps.

In the reagent replacement position transferring steps 103 shown in FIG. 5, the replacement reagent container holding mechanism 10 is rotated so that the reagent replacement position transferring mechanism 12 and the standby position of the replacement reagent container 20 moving within the replacement reagent container holding mechanism 10 are on a straight line. Next, the replacement reagent container 20 is moved by using the reagent replacement position transferring mechanism 12. The reagent replacement position transferring mechanism 12 is composed of a reagent replacement position transferring support part 12-1 and a reagent replacement position transferring mechanism driving motor 12-2. The reagent replacement position transferring mechanism driving motor 12-2 is operated to convert, by the motor operation thereof, the operation of the reagent replacement position transferring support part 12-1 into linear movement, and the replacement reagent container 20 is moved to the reagent replacement position transferring mechanism 12. In this way, the position of the replacement reagent container holding mechanism 10 is vacated to again receive another replacement reagent container 20.

Although not shown in the drawings, after the above-described operation, an operation is performed in which the replacement position transferring mechanism driving motor 12-2 is revolved in the reverse direction, and the reagent replacement position transferring support part 12-1 is moved to the initial position.

By causing steps 101, steps 102 and steps 103 to sequentially take place, the replacement reagent container 20 can be moved to the replacement position. However, since the replacement reagent container holding mechanism 10 is rotated, a replacement reagent container 20 is on the straight line with the reagent replacement position transferring mechanism 12 while another replacement reagent container 20 is subjected to the opening operation, Then, the rotations of replacement reagent container holding mechanism 10 in steps 101, steps 102 and steps 103 are determined to be one independent step 200 and referred respectively as steps 201, steps 202, step 203 that are independent. This makes it possible, at the point where the operation of step 200 is completed, to perform steps 201, steps 202 and step 203 simultaneously.

Figure 6:
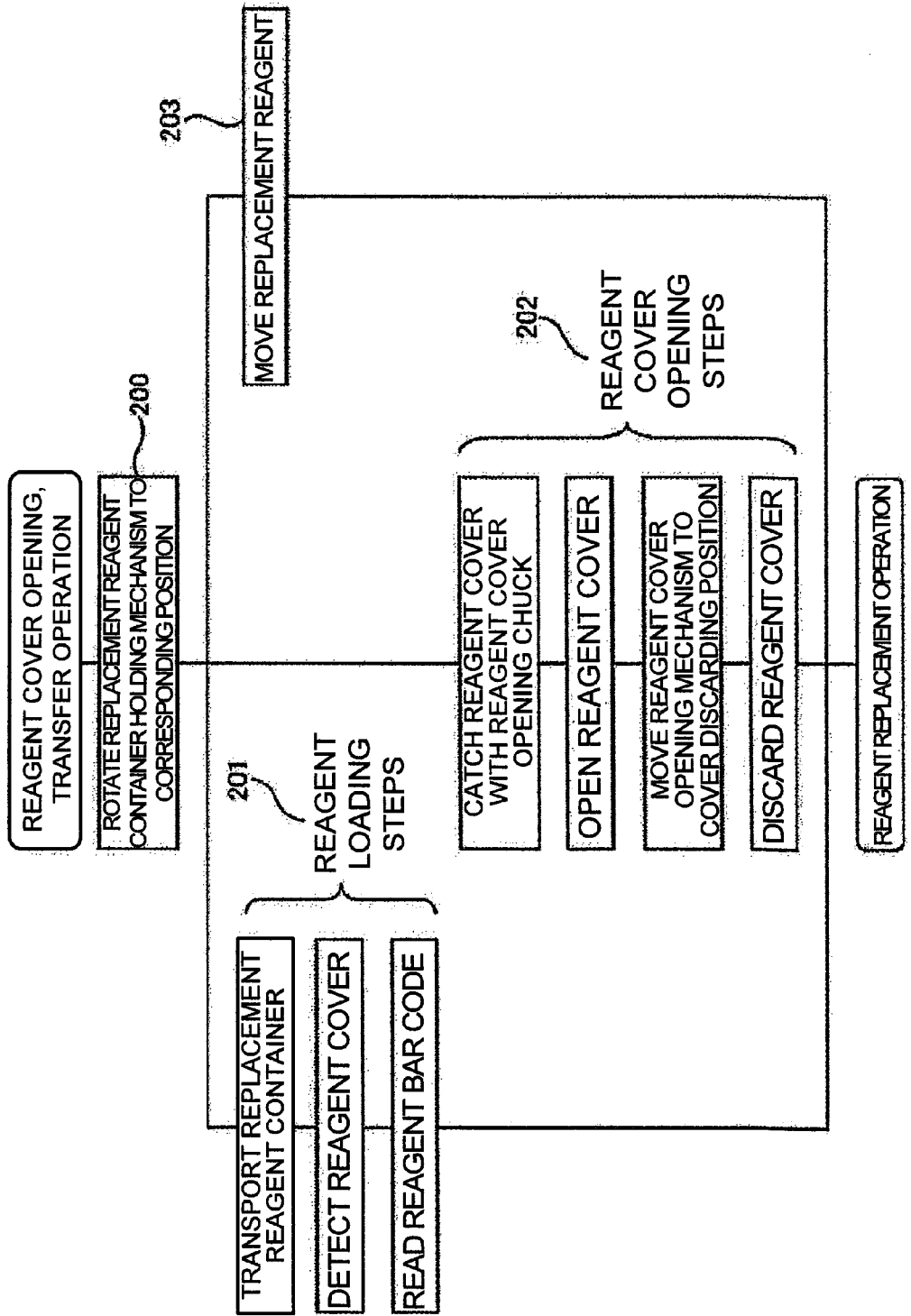
FIG. 6 shows steps of causing a reagent cover opening operation and a reagent transferring operation to function in parallel with each other.

Here, when one replacement reagent container 20 is focused on, it is assumed that the replacement reagent container 20 is usually loaded before an inspection in the morning is initiated. That is, as shown in FIG. 6, it can be considered that the action of the reagent loading steps 201 is rarely performed during the time when the device is being operated. On the other hand, it is desirable that the reagent cover 22 of the replacement reagent container 20 is kept unopened until immediately before the actual use of the device. This is in order to suppress the change of a reagent concentration caused by vaporization of the reagent filled in the replacement reagent container 20 as far as possible. Then, it can be said that it is desirable that the reagent cover opening steps 202 and the reagent replacement position transferring step 203 for one replacement reagent container 20 are continuously performed.

The replacement reagent container holding mechanism 10 of the present invention for continuously performing the reagent cover opening steps 202 and the reagent replacement position transferring step 203 will be explained.

The replacement reagent container holding mechanism 10 shown in FIG. 1 has at the maximum 10 (ten) holding slots, and the reagent cover opening mechanism 11 and the reagent replacement position transferring mechanism 12 are radially arranged with respect to the replacement reagent container holding mechanism 10, and has a position that is offset by 3 slots in the counterclockwise direction. That is, the mechanisms 11 and 12 have offsets of 3 slots in between them. The number, 10 (ten), of the reagent containers held by the replacement reagent container holding mechanism, and the offset of the mechanism arrangement, 3 (three), are in an undividable numerical relationship, which is 10=3×3+1. By being designed so, if the replacement reagent containers 20 are loaded in succession on another reagent container holding mechanism or another analysis unit that is not illustrated and arranged in succession at positions with three offsets between the replacement reagent containers in the clockwise direction, it is possible to continuously perform the above-stated movement from the reagent cover opening to the reagent replacement positions. Further, by arranging the reagent containers in this way, opening the reagent container covers and loading the reagent containers to another reagent holding mechanism or analysis unit can be preformed substantially at the same timing to thereby minimize the rotation of the replacement reagent container holding mechanism 10.

Figure 7:
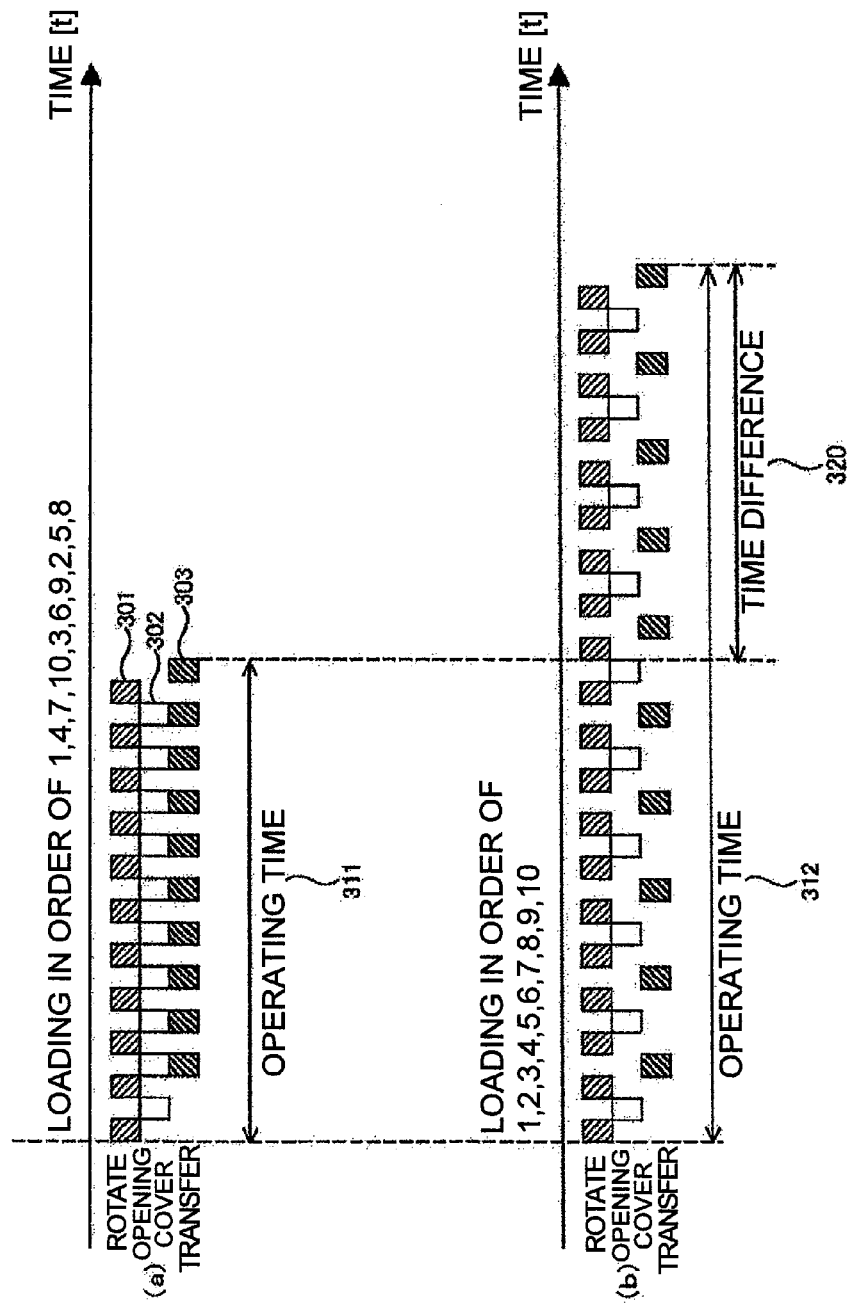
FIG. 7 shows a difference in operating time in successively loading reagent to the analyzer unit.

For example, when a reagent container whose cover has been opened and disposed in a slot 1 is loaded to another reagent container holding mechanism or another analysis unit by the reagent replacement position transferring mechanism, the reagent of slot 4 is moved to the position where the reagent cover opening mechanism performs the cover opening. That is, when the slots are numbered as 1, 2, 3 in the clockwise rotation, by placing the reagents in the slots in the order of 1, 4, 7, 10, 3, 6, 9, 2, 5, 8, it is possible, as shown in FIG. 7 (a), to cause the reagent cover opening mechanism 11 and the reagent replacement position transferring mechanism 12 to operate substantially at the same timing. This makes it possible to suppress the number of times of rotation operation of the replacement reagent container holding mechanism 10 to minimum, and reduce the total time required for loading a reagent to another reagent holding mechanism or analysis unit. Further, it thereby is possible to suppress bubbling in the liquid surface of the reagent.

Further, since a reagent container transported by the reagent replacement position transferring mechanism 12 at one cycle is the reagent container whose cover is opened by the reagent cover opening mechanism 11 at the cycle preceding thereto, it is possible to continuously perform the movement from the reagent cover opening to the reagent replacement position.

On the other hand, FIG. 7 (b) shows the timing of the operation of the conventional mechanisms. Since the reagent cover opening mechanism 11 and the reagent replacement position transferring mechanism 12 are performed in different timings, it is necessary to rotate the replacement reagent container holding mechanism 10 each time therefor, and the total of the necessary process time will be extended. Further, since the rotation number of the replacement reagent container holding mechanism 10 increases, it is likely that bubbling in the liquid surface of the reagent is caused.

In order to achieve the operation shown in FIG. 7 (a), there are two possible methods.

The replacement reagent holding mechanism 10 shown in the present embodiment is principally managed to receive in advance the disposing of the replacement reagent containers 20 for use in one day. Therefore, when the replacement reagent container 20 is loaded from one replacement reagent holding mechanism 10 to another reagent container holding mechanism or analysis unit, the position of a vacant slot is determined so that continuous loading of the replacement reagent containers 20 can be achieved.

One method resides in optimally selecting the slot position number at disposing the replacement reagent container 20 in the replacement reagent container holding mechanism 10.

Figure 8:
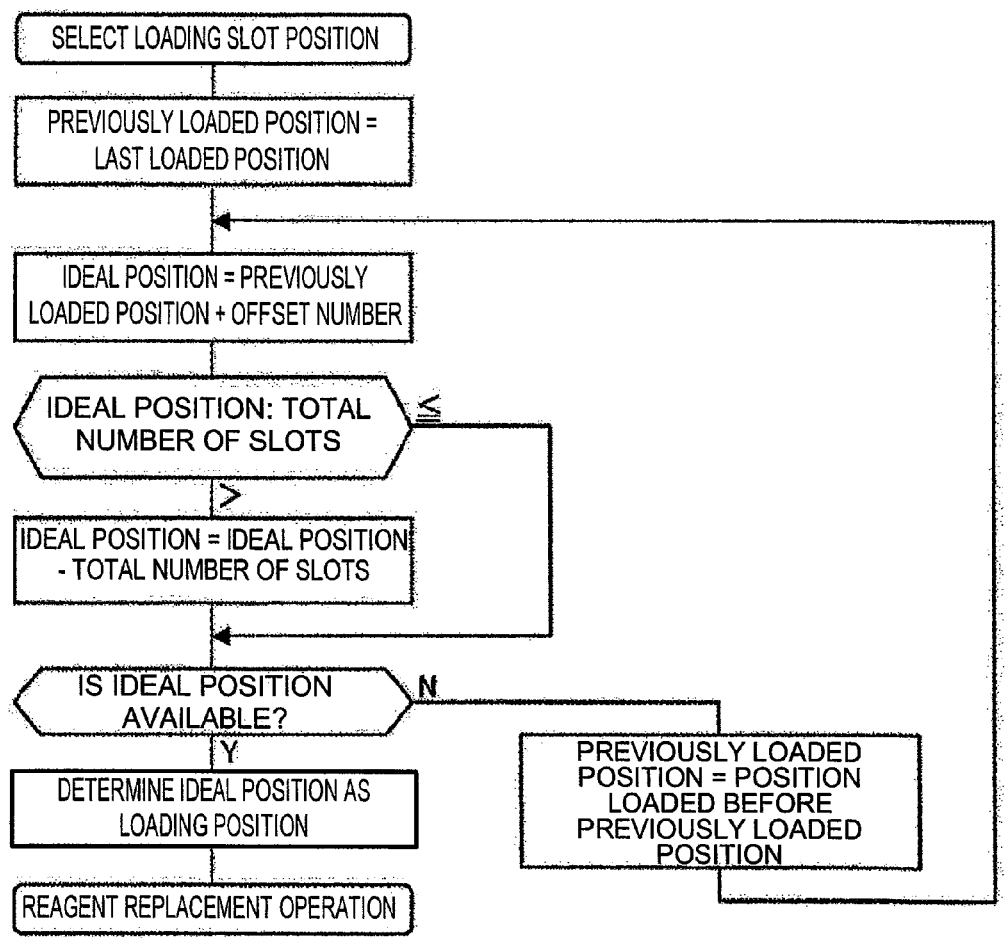
FIG. 8 shows a flowchart in which the loading position for loading a reagent container is determined.

Referring to FIG. 8 for explanation, each replacement reagent container 20 has its reagent container loaded time recorded. In the information, the slot position number where the last replacement reagent container 20 is loaded is registered as a previously loaded position.

A value obtained by adding the offset number of the mechanism to the previously loaded position is determined as an ideal position.

When the ideal position is greater than the total number of slots, the total number of slots is subtracted from the ideal position.

Determination is made as to whether the slot shown by the ideal position is available, and if it is available, the slot number is determined as a loading position.

If the slot is not available, a slot position registered before the time when the replacement reagent container 20 has been loaded at the previously loaded position is updated as another previously loaded position and the same process is repeated.

In this way, when all the slots are available, all the replacement reagent containers 20 are loaded in the successive positions. Further, even when some of the slots are already filled with disposed containers, it is possible to establish a successive positional relationship with respect to the lastly disposed reagent.

Of course, although it is not described in the present embodiment, the logic for selecting a loading slot position is not executed unless any loadable slot is available.

As another method, there is an implementation in which the cover of a replacement reagent container 20 is actually opened, and which is achieved by scheduling at the time of moving the replacement reagent container 20 to another reagent container holding mechanism or analysis unit.

Figure 9:
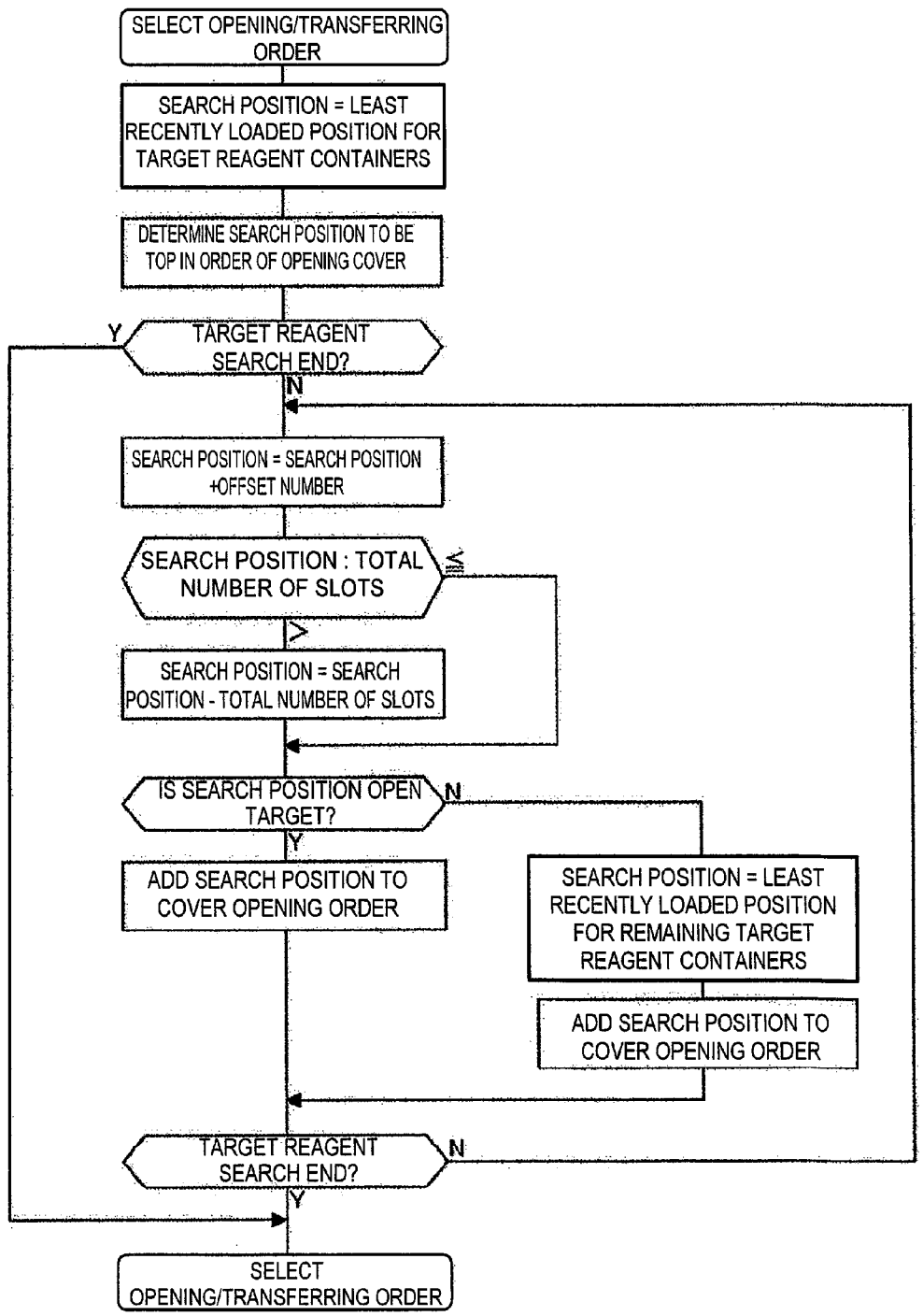
FIG. 9 shows a flowchart for in which the order of operations for reagent container opening and reagent container movement is determined.
Figure 10:
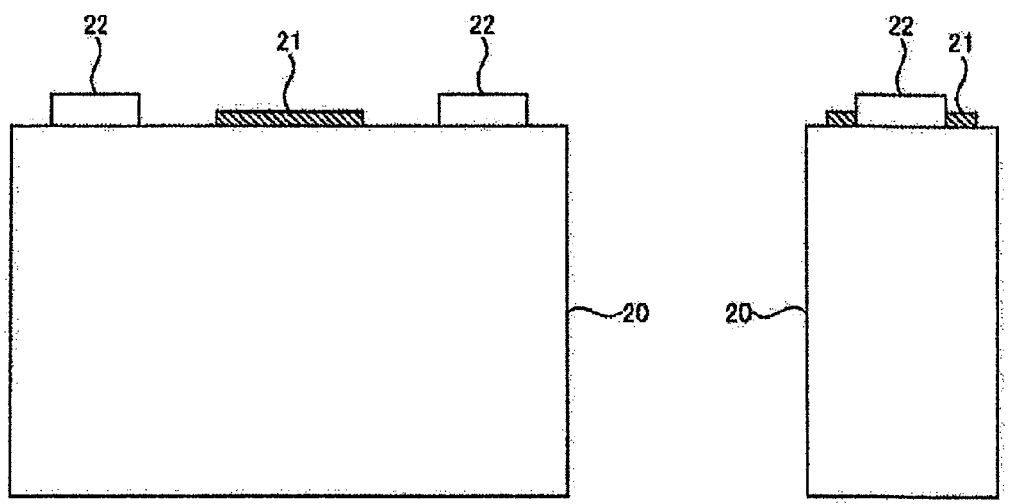
FIG. 10 is a trihedral figure showing a replacement reagent container used in one embodiment of the present invention.
Figure 10:
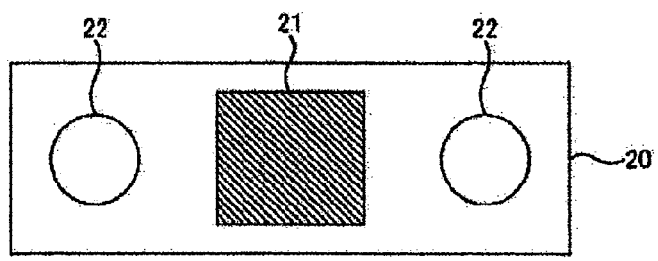

Refereeing to FIG. 9 for explanation, first, an instruction of request for opening the cover and transfer of the replacement reagent container 20 is given by the microcomputer 1 via an interface 6. In this phase, cover opening and transfer are instructed for a plurality of replacement reagent containers 20.

Since each replacement reagent container 20 has its reagent container loaded time recorded, the slot position where the oldest replacement reagent container 20 of the target replacement reagent containers 20 has been disposed is registered as a search position and scheduled to be first opened and moved.

At this time, if only 1 (one) reagent container is to be subjected to cover opening and transfer, the process terminates.

Next, a numeric value obtained by adding the offset number of the mechanism to the search position is determined as the next search position.

When the search position is greater than the total number of slots, the total number of slots is subtracted from the search position.

When the slot shown by the search position is the cover opening and transfer object, the search position is added to a scheduled order for cover opening and movement.

When the slot shown by the search position is not to be subjected to the cover opening and transfer, the one that was loaded least recently of the remaining target reagent containers is added to the scheduled order according to which cover opening and transfer is performed.

As long as any target reagent container is present, the offset is added to repeat the logic to determine the scheduled order.

In this way, when all the replacement reagent containers 20 are subjected to cover opening and movement, all the replacement reagent containers 20 are to be subjected to cover opening and movement in a continuous sequence. Further, even when replacement reagent containers of some of the slots are not the target, and there occurs vacancy temporarily at that time, it is possible to achieve scheduling that is continuous in other parts.

That is, when the replacement reagent container holding mechanism 10 is denoted as X, and the offset number of the reagent cover opening mechanism 11 and the reagent replacement position transferring mechanism 12 is denoted as Y, when the mechanism is arranged such that a relationship $X=nY+1$ (n is an arbitrary natural number except for 0) establishes, an operation shown in the present embodiment is made possible, and it is possible to achieve continuous scheduling and reduction of number of times of operation of the mechanism. Further, it is possible to provide an automatic analyzing device that, by reducing the number of times of the operation, can reduce the speed of the operation and suppress bubbling in the liquid surface and rolling of the liquid surface.

Further, the relationship establishes also when $X=nY-1$. For instance, when the offset number Y of the mechanism is determined as 3 according to the above-described embodiment, X is 8. In this case, the reagent may be disposed in the order of the sequence: 1, 4, 7, 2, 5, 8, 3, 6.

Furthermore, the relationship establishes when $X=nY\pm m$, where m can be any natural number except for 0 and other than the divisors of Y.

REFERENCE SIGNS LIST 1 microcomputer
2 memory employed by microcomputer
3 external storage medium
4 keyboard
5 display
6 interface
10 replacement reagent container holding mechanism
10-1 replacement reagent container holding mechanism driving motor
11 reagent cover opening mechanism
11-1 reagent cover opening chuck
11-2 reagent cover discarding box
12 reagent replacement position transferring mechanism
12-1 reagent replacement position transferring support part
12-2 reagent replacement position transferring mechanism driving motor
13 reagent container loading mechanism
14 reagent discarding mechanism
15 reagent bar code reading mechanism
16 reagent cover detection mechanism
20 replacement reagent container
20-1, 20-2, 20-3, 20-4 replacement reagent container on stand-by
21 reagent bar code
22 reagent cover
101, 201 reagent loading steps
102, 202 reagent cover opening steps
103, 203 reagent replacement position transferring step(s)
200 replacement reagent container holding mechanism rotation step
210 reagent loading position determination steps
301 replacement reagent container holding mechanism rotation operation time
302 reagent cover opening mechanism operation time
303 reagent replacement position transferring mechanism operation time
311 operating time in the continuous reagent loading operation after optimization
312 operating time in the continuous reagent loading operation before optimization
320 difference in the operating time in the continuous reagent loading operation

The invention claimed is:

1. An automatic analyzing device comprising:
an analysis unit that analyzes samples;
a rotatable reagent container holding mechanism that holds a plurality of reagent containers placed thereon;
a reagent replacement position transferring mechanism that transfers the reagent containers placed on the reagent container holding mechanism held at a reagent replacement position to the analysis unit located outside of the reagent container holding mechanism;
a reagent container loading mechanism that loads the reagent containers on to the reagent container holding mechanism;
a reagent cover opening mechanism that opens covers of the reagent containers on the reagent container holding mechanism held at a reagent cover opening position; and
a processor interfaced with the reagent container holding mechanism, the reagent replacement position transferring mechanism, the reagent container loading mechanism, and the reagent cover opening mechanism,
wherein the processor is programmed to control:
the reagent container holding mechanism to rotate to move the reagent containers between the reagent cover opening position and the reagent replacement position so that a number of slots (Y) of the reagent container holding mechanism by which ones of the reagent containers held at the reagent cover opening position move between the reagent cover opening position and the reagent replacement position satisfies a relationship of $X=nY\pm1$ (where n is an arbitrary natural number except for 0 and X is a reagent container holding capacity of the reagent container holding mechanism), and
the reagent replacement position transferring mechanism to transfer a first one of the reagent containers, the cover of which has been opened by the reagent cover opening mechanism at the reagent cover opening position and has been moved from the reagent cover opening position to the reagent replacement position by rotating the reagent container holding mechanism, from the reagent replacement position to the analysis unit located outside of the reagent container holding mechanism simultaneously with the reagent cover opening mechanism to open a cover of a second one of the reagent containers on the reagent container holding mechanism at the reagent cover opening position.

2. The automatic analyzing device according to claim 1, wherein the processor is further programmed to control:

the reagent container holding mechanism to rotate to move the reagent containers between the reagent cover opening position and the reagent replacement position so that the number of slots (Y) by which ones of the reagent containers held at the reagent cover opening position move between the reagent cover opening position and the reagent replacement position satisfies the relationship of X=nY±m (where n is an arbitrary natural number except for 0, X is the reagent container holding capacity of the reagent container holding mechanism, and m is an arbitrary natural number except for 0 and except for divisors of Y).

3. The automatic analyzing device according to claim 2, wherein the processor is further programmed to control:

the reagent container loading mechanism to rotate in a direction opposite to a direction in which the ones of the reagent containers move by the number of slots (Y) during a period in which the one of the reagent containers is loaded on to the reagent container holding mechanism.

4. The automatic analyzing device according to claim 1, wherein the processor is further programmed to control:

the reagent container loading mechanism to rotate in a direction opposite to a direction in which the ones of the reagent containers move by the number of slots (Y) during a period in which one of the reagent containers is loaded on to the reagent container holding mechanism.

5. The automatic analyzing device according to claim 1, further comprising:

a reagent cover opening and closing detection mechanism that detects whether covers provided on the reagent containers are open or closed, and wherein the processor is connected to and further programmed to control the reagent cover opening and closing detection mechanism.

6. The automatic analyzing device according to claim 1, wherein, the reagent container holding mechanism comprises a reagent bar code reading mechanism that reads reagent bar codes affixed to the reagent containers.

7. The automatic analyzing device according to claim 1, wherein, the reagent container holding mechanism comprises a reagent discarding mechanism that discards a reagent container determined to be unusable.

8. The automatic analyzing device according to claim 1, wherein the processor is further programmed to control:

the reagent container holding mechanism to rotate such that after the covers of the reagent containers held at the reagent cover opening position are opened by the reagent cover opening mechanism, the reagent containers are moved to the reagent replacement position.

9. The automatic analyzing device according to claim 1, wherein the processor is further programmed to control:

the reagent container holding mechanism so that opening of reagent containers by the reagent cover opening mechanism and placing of reagent containers on the reagent replacement position transferring mechanism are performed simultaneously, and the reagent container holding mechanism to rotate and the reagent container loading mechanism to load reagent containers so that a subsequent reagent container is loaded at a position separated by Y slots from a position where a previous reagent container had been located prior to placement at the reagent replacement position.

10. The automatic analyzing device according to claim 1, wherein the processor is further programmed to control:

the reagent cover opening mechanism to open the cover of one of the reagent containers in a loaded state on the reagent container holding mechanism;

the reagent container holding mechanism rotates and moves the reagent container having its cover opened for Y slots to the reagent replacement position; and the reagent replacement position transferring mechanism transfers the reagent container having its cover opened and moved by rotation of the reagent container holding mechanism to the reagent replacement position to the analysis unit located outside of the reagent container holding mechanism.

11. The automatic analyzing device according to claim 1, wherein the processor is further programmed to control:

the reagent container holding mechanism to rotate by the number of slots (Y) in each rotation thereof.

12. The automatic analyzing device according to claim 1, wherein the processor is further programmed to control:

the reagent replacement position transferring mechanism to transfer a first one of the reagent containers, the cover of which has been opened by the reagent cover opening mechanism at the reagent cover opening position and has been moved from the reagent cover opening position to the reagent replacement position by rotating the reagent container holding mechanism, from the reagent replacement position to the analysis unit located outside of the reagent container holding mechanism simultaneously with the reagent cover opening mechanism to open a cover of a second one of the reagent containers on the reagent container holding mechanism at the reagent cover opening position and simultaneously with the reagent container loading mechanism to load a third one of the reagent containers on to the reagent container holding mechanism.

* * * * *